United States Patent
Bukhary et al.

(10) Patent No.: US 9,872,744 B2
(45) Date of Patent: Jan. 23, 2018

(54) ORTHODONTIC BRACKET

(71) Applicant: KING SAUD UNIVERSITY, Riyadh (SA)

(72) Inventors: Mohammed Taher Mulla Akram Bukhary, Riyadh (SA); Ferdous Mohammed Taher Mulla Akram Bukhary, Riyadh (SA); Sahar Faisal Sharaf Albarakati, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/084,432

(22) Filed: Mar. 29, 2016

(65) Prior Publication Data
US 2017/0281317 A1   Oct. 5, 2017

(51) Int. Cl.
*A61C 7/14* (2006.01)
*A61C 7/16* (2006.01)

(52) U.S. Cl.
CPC .............. *A61C 7/146* (2013.01); *A61C 7/143* (2013.01); *A61C 7/148* (2013.01); *A61C 7/16* (2013.01)

(58) Field of Classification Search
CPC .. A61C 7/12; A61C 7/14; A61C 7/141; A61C 7/143; A61C 7/145; A61C 7/148; A61C 7/16; A61C 7/146
USPC ........................................ 433/8, 9, 10, 16, 17
See application file for complete search history.

(56) References Cited

U.S. PATENT DOCUMENTS

| | | | |
|---|---|---|---|
| 5,125,832 A * | 6/1992 | Kesling | A61C 7/12 433/16 |
| 5,238,402 A * | 8/1993 | Rohlcke | A61C 7/12 29/896.11 |
| 5,326,259 A | 7/1994 | Rahlcke et al. | |
| 6,276,930 B1 | 8/2001 | Pozzi | |
| 6,478,579 B1 * | 11/2002 | Brusse | A61C 7/12 433/10 |
| 7,175,428 B2 | 2/2007 | Nicholson | |
| 7,641,472 B2 * | 1/2010 | Sears | A61C 7/14 433/8 |
| 7,677,887 B2 * | 3/2010 | Nicholson | A61C 7/28 433/11 |
| 8,678,817 B2 | 3/2014 | Stevens | |

(Continued)

FOREIGN PATENT DOCUMENTS

| CN | 201418789 Y | 3/2010 |
|---|---|---|
| CN | 203591343 U | 5/2014 |
| WO | WO 2010/114692 A1 | 10/2010 |

OTHER PUBLICATIONS

"Damon 3MX Marking System," OrmcoTM Orthodontic Products Catalog, section I, p. 8, © 2013.

*Primary Examiner* — Nicholas Lucchesi
(74) *Attorney, Agent, or Firm* — Richard C. Litman (57) ABSTRACT

The orthodontic bracket includes a base and a bracket body extending from the base. The bracket body includes a lower labial surface on which a first indicia is displayed and a plurality of tie-wings extending from corner portions of the base on which a second indicia is displayed. The labial surfaces face the patients lips, once positioned on the patient's tooth. The first indicia can be a number corresponding to a specific tooth in a patient's mouth to which the bracket is designed to attach. The second indicia can be a dot positioned on a tie-wing associated with a specific quadrant of the patient's mouth.

4 Claims, 8 Drawing Sheets

(56) References Cited

U.S. PATENT DOCUMENTS

| | | | | |
|---|---|---|---|---|
| 2002/0150857 A1* | 10/2002 | Orikasa | .................... | A61C 7/14 |
| | | | | 433/8 |
| 2006/0166158 A1* | 7/2006 | Abels | ....................... | A61C 7/14 |
| | | | | 433/8 |
| 2006/0166159 A1* | 7/2006 | Abels | ....................... | A61C 7/14 |
| | | | | 433/8 |
| 2007/0224569 A1* | 9/2007 | Oda | ......................... | A61C 7/02 |
| | | | | 433/10 |
| 2009/0286195 A1* | 11/2009 | Sears | ....................... | A61C 7/14 |
| | | | | 433/8 |
| 2009/0291404 A1* | 11/2009 | Oda | ....................... | A61C 7/287 |
| | | | | 433/11 |
| 2010/0129765 A1* | 5/2010 | Mohr | ....................... | A61C 7/12 |
| | | | | 433/10 |
| 2012/0315594 A1* | 12/2012 | Ehrenberger | ............ | A61C 7/14 |
| | | | | 433/9 |
| 2014/0099593 A1 | 4/2014 | Bingmin et al. | | |
| 2014/0212827 A1* | 7/2014 | Tzou | ..................... | A61C 7/146 |
| | | | | 433/8 |

* cited by examiner

ORTHODONTIC BRACKET

BACKGROUND OF THE INVENTION

1. Field of the Invention

The present invention relates to orthodontic devices, and particularly to orthodontic brackets including indicia on a labial surface thereof that is visible to the naked eye.

2. Description of the Related Art

Straight-wire brackets are used in conjunction with a series of preformed arch wires to move teeth to their desired location in the arch form. Each of the brackets are configured to have the ideal tip, torque, angulation, and in/out position for a specific tooth. Practitioners generally rely on tiny indicia, such as dots, color spots, as well as the overall shape, size, and morphology of the particular bracket to match a bracket to the correct tooth. However, since the brackets themselves are extremely small devices, there is very little space on the labial surface of the bracket to display indicia in a size that is easily recognizable with the naked human eye. A mistake in bracket identification and selection can result in attaching a dental bracket to an incorrect tooth, which can lead to wrong tooth positioning and angulation, resulting in a failure of treatment.

Thus, an orthodontic bracket with sufficient space on a labial surface thereof to include identification indicia that is large enough to be visible to the naked eye is desired.

SUMMARY OF THE INVENTION

The orthodontic bracket includes a base and a bracket body extending from the base. The bracket body includes a lower labial surface on which a first indicia is displayed and a plurality of tie-wings extending from corner portions of the base on which a second indicia is displayed. The labial surfaces face the patients lips, once positioned on the patient's tooth. The first indicia can be a number corresponding to a specific tooth in a patient's mouth to which the bracket is designed to attach. The second indicia can be a dot or other indicia. The tie-wing including the second indicia is associated with a specific quadrant of the patient's mouth in which the bracket is to be positioned.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
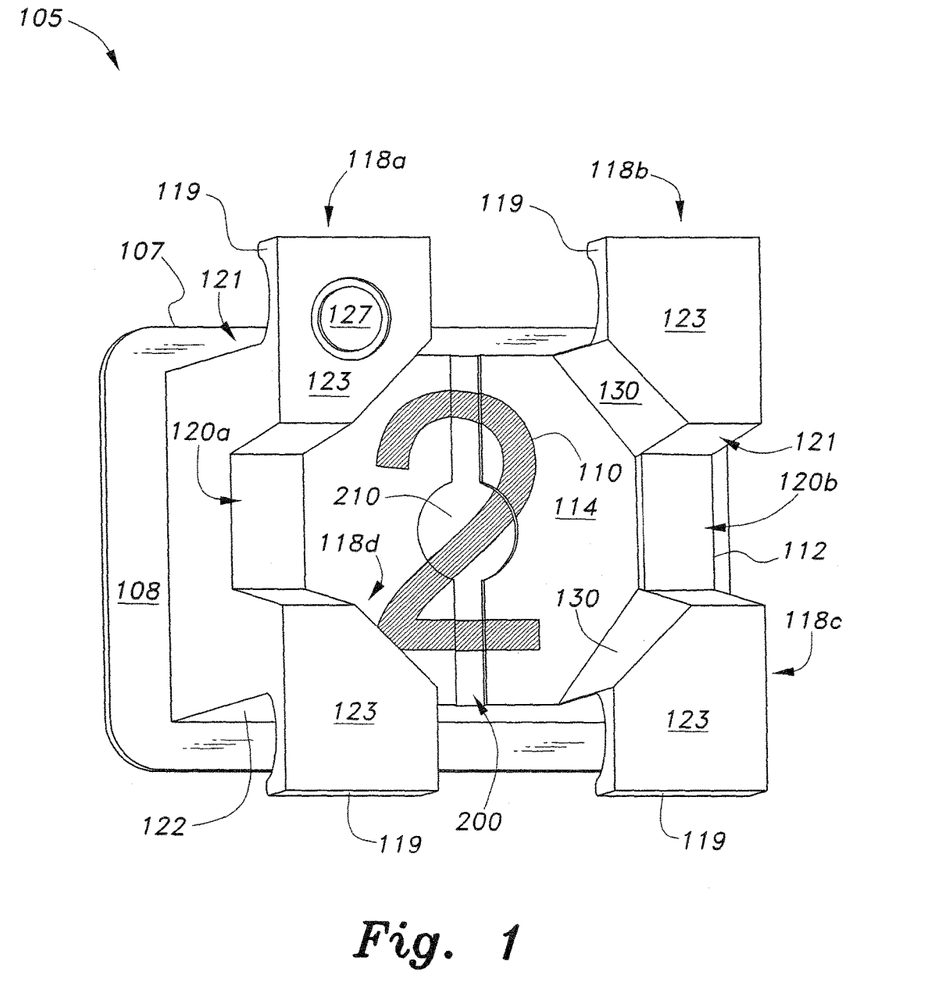
FIG. 1: is an environmental, front view of an orthodontic bracket, according to the present invention.
Figure 2:
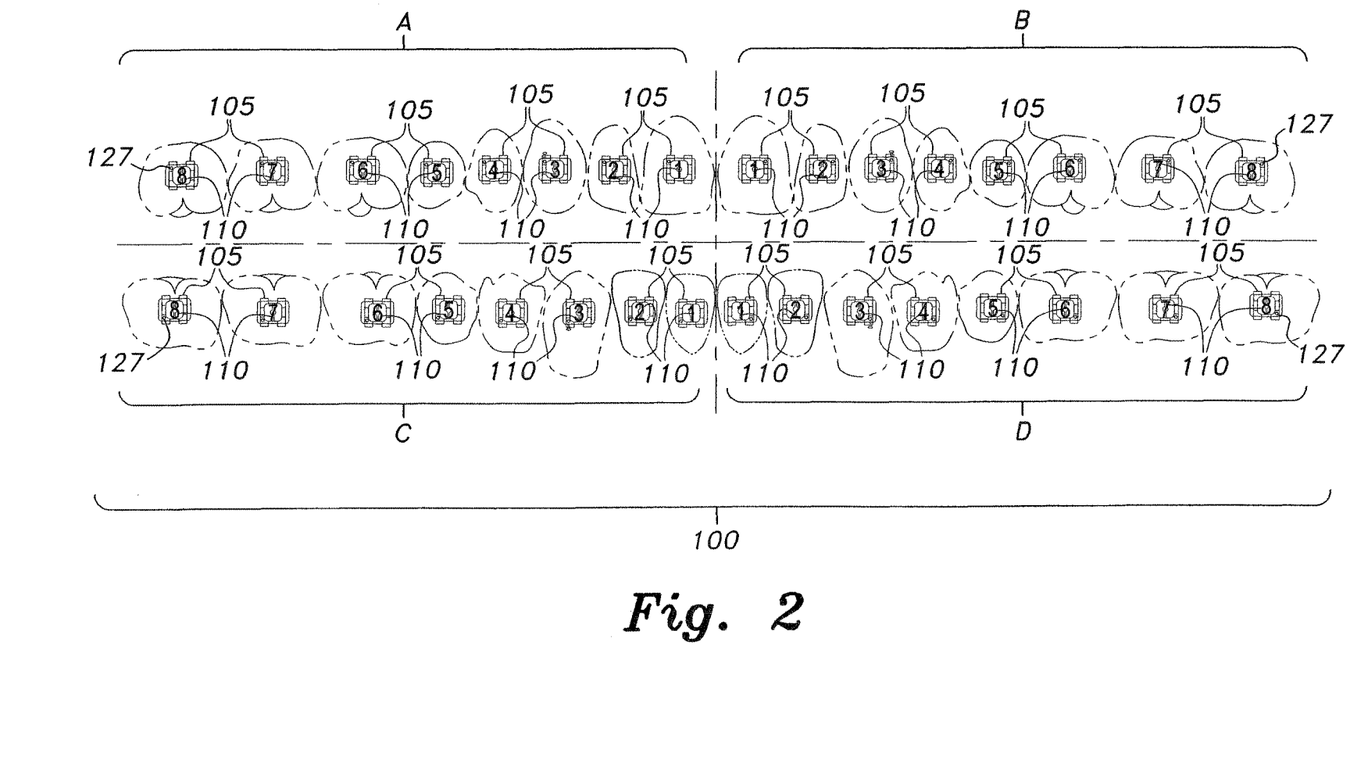
FIG. 2 is an environmental view of a set of orthodontic brackets positioned on a patient's teeth, according to the present invention.

Referring to FIG. 1, an orthodontic bracket 105 includes a base 107 having a rear surface (not shown) configured for attachment onto a tooth surface TS, and an opposing front surface 108 from which a bracket body 112 extends. The bracket body 112 includes a lower labial surface 114 on which a first indicia 110 is displayed. The lower labial surface 114 can be defined by an exposed, lower horizontal surface of the body 112, which faces the patient's lips once the bracket is positioned on the patient's tooth. The lower labial surface 114 is open and visible to a practitioner working with the bracket 105. In other words, other portions of the bracket 105 do not obstruct the lower labial surface 114 from view, thereby allowing indicia displayed thereon to be visible to the practitioner. The first indicia 110 can be a number corresponding to a specific tooth T in a patient's mouth to which the bracket is designed to attach. FIG. 2 shows a set of orthodontic brackets positioned on a patient's teeth, according to the present invention.

Figure 3:
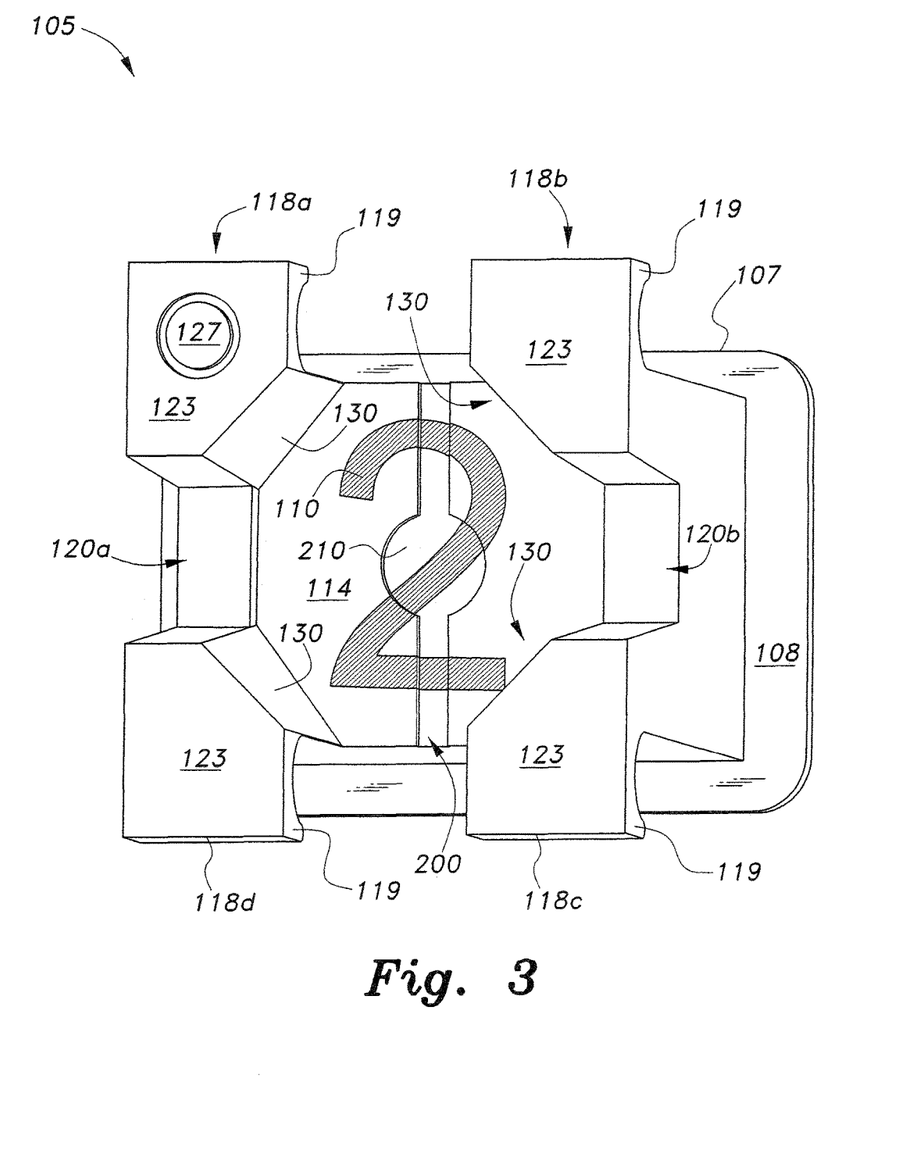
FIG. 3 is a right-side perspective view of an orthodontic bracket, according to the present invention.

Referring to FIGS. 1 and 3, a plurality of outwardly extending hooks or tie-wings protrude from corners of the bracket body 112, and are higher than or further from the base 107 than the lower labial surface 114. The tie-wings can include a disto-gingival tie-wing 118a, a mesio-gingival tie-wing 118b, a mesio-occlusal tie-wing 118c, and a disto-occlusal tie-wing 118d. A first slot 120a is formed between the disto-gingival tie wing 118a and the disto-occlusal tie-wing 118d. A second slot 120b is formed between the mesio-gingival tie-wing 118b and the mesio-occlusal tie-wing 118c. The first and second slots 120a and 120b are horizontally aligned and configured for receiving different portions of an arch wire therein. Each tie-wing 118a-118b includes an upright shaft 121, an upper labial surface 123 extending normal to the shaft 121, and a lip 119 depending from the upper labial surface 123. The lip 119 can extend away from the base. The upper labial surface 123, like the lower labial surface 114, is open and unobstructed. The upper labial surface 123 of one of the tie-wings 118a-118d on each bracket 105 includes a second indicia 127. The second indicia 127 can include a dot or other indicia. The tie-wing including the second indicia corresponds to the quadrant, such as the upper left quadrant A, the upper right quadrant B, the lower right quadrant C, or the lower left quadrant D, of the patient's mouth in which the bracket should be positioned (FIG. 2). For example, a dot on the upper left tie-wing indicates that the bracket should be positioned in the upper left quadrant A. A dot on the upper right tie-wing indicates that the bracket should be positioned in the upper right quadrant B. A dot on the lower right quadrant C indicates that the bracket should be positioned in the lower right quadrant C. A dot on the lower left quadrant D indicates that the bracket should be positioned in the lower left quadrant D.

Each shaft 121 includes a plurality of upright sides 122. An inner, upright side 130 of the plurality of upright sides 122 faces an inner upright side 130 of a diagonally opposed tie-wing shaft 121. For example, the inner upright side 130 of the disto-gingival tie-wing 118a faces the inner upright side 130 of the mesio-occlusal tie-wing 118c. The inner upright side 130 of the mesio-gingival tie-wing 118b faces the inner upright side 130 of the disto-occlusal tie wing 118d. As such, the tie-wings can lack a corner or corner portion that extends on or over the lower labial surface 114.

Figure 4:
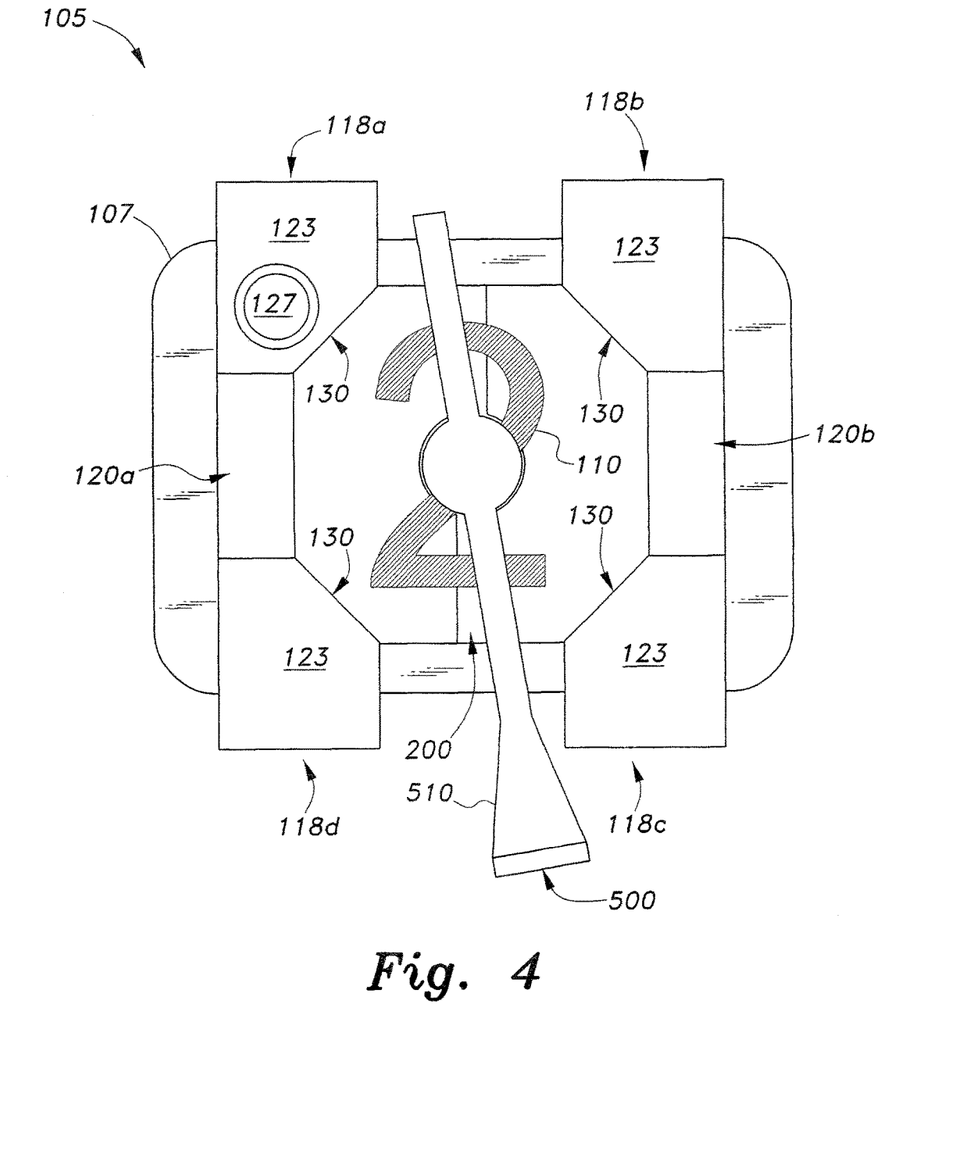
FIG. 4 illustrates the bracket positioning key for repositioning an orthodontic bracket, according to the present invention.

As depicted in FIG. 3, the lower labial surface 114 of the body 112 includes a generally linear occluso-gingival opening 200 with a generally circular centering guide opening 210 at the center of the occluso-gingival opening 200. The occluso-gingival opening 200 can be key-hole shaped and extend longitudinally along a central portion of the lower labial surface 114 of the body 112 of each bracket 105. The centering guide opening 210 can be generally positioned at a center of each bracket 105 so as to provide a reference or guide for bracket positioning. The occluso-gingival opening 200 can receive a bracket positioning key 500 (FIG. 4). The key includes a handle 510 that can be manipulated to facilitate bracket positioning or movement, e.g., rotational, lateral, or vertical movement of the bracket, until the correct bracket positioning is achieved. Once the correct bracket positioning is achieved, a bonding agent is allowed to set.

The base 107 of the orthodontic bracket 105 can be formed from any suitable material, such as stainless steel or titanium. The rear surface of the base 107 can have a concave shape so as to match the convex surface of the labial surface of the corresponding matching tooth T. Further, the rear surface of the base 107 can include a retentive layer, such as a foil mesh or a layer of grooves, suitable for holding the bonding agent, such as cement, for attaching the rear side of the body 107 to the tooth T, such as directly onto the enamel of the labial surface of the corresponding tooth T.

Figure 5:
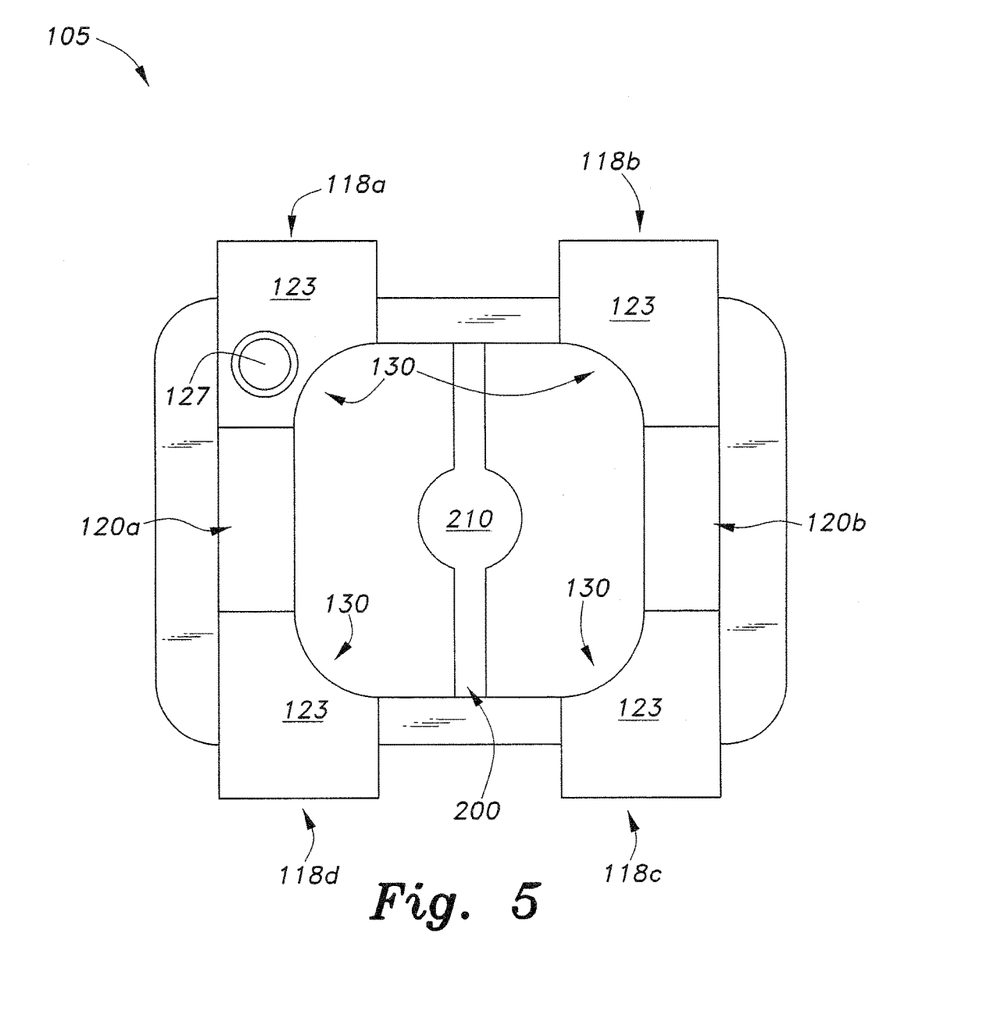
FIG. 5 is another embodiment of an orthodontic bracket, according to the present invention.

Each tie-wing 118a-118d can have straight edges as illustrated in FIG. 3, or can have at least one curved edge, as illustrated in FIG. 5. As shown in FIGS. 3 and 5, however, corners of the tie-wings 118a-118d do not extend into the labial surface 114 of the body 112. As such, more of the labial surface 114 of the bracket 105 is exposed than conventional brackets. Thus, any indicia displayed on the labial surface 114 can be made larger than those displayed on conventional brackets. Further, the shaft configuration of the tie wings 118a-118d reduces the total contact area between the shaft and the archwire AW; thereby decreasing friction and minimizing the chance of chafing that typically occurs with conventional brackets. The frontal profile of each bracket 105 configured for the upper central incisors, later incisors, canines and lower canines can be rhomboidal, whereas the frontal profile of each bracket 105 configured for the upper and lower premolars and lower incisors can be rectangular.

As illustrated in FIG. 2, the first indicia can include the numbers 1 to 8, while the second indicia 127 can include the letters A-D. The first indicia 110 can be displayed on the visible portion of the lower labial surface 114, while the second indicia 127 can be defined on the visible upper labial surface 123 of any one of the tie-wings. The size of the first indicia 110 and the second indicia 127 can be large enough to be seen, read, and/or recognized by the naked human eye without the need for a magnifying glass. The first indicia 110 and the second indicia 127 can be temporary or permanent. For example permanent laser printing or a temporary ink that is washable can be used for the first indicia 110 and/or the second indicia 127. Permanent laser printing or other permanent indicia can be particular useful after the bracket has been positioned, e.g., in helping examining dental professionals determine whether each bracket 105 has been matched to the correct tooth T or whether the first indicia 110 on the labial surface 114 of the body 112 overlaps the central part of the clinical crown of the tooth T. Also, once the bracket is properly positioned on the tooth, the degree of visibility or appearance of the permanent mark can indicate to the patient whether or not food debris and/or plaque is accumulating thereon. This can serve to encourage additional tooth cleaning, such as tooth brushing and overall oral hygiene.

The archwire slots 120a and 120b can extend in a horizontal mesial-distal direction along the body 112, as illustrated in FIGS. 3 and 5. The archwire slots 120a and 120b can have any suitable dimensions (ie. slot size), such as 0.018 or 0.022 inches. The slot size can be configured to accommodate the width of the archwire. The depth of the archwire slots 120a and 120b can be 0.025 inches for the 0.018 inch archwire slot and 0.028 inches for the 0.022 inch archwire slot 120. Thus, the brackets 105 can be manufactured with the standard 0.018×0.025 inch and 0.022×0.028 inch slot size and provided with prescribed tip and torque values in accordance with a selected prescription and made available to orthodontists.

Figure 6:
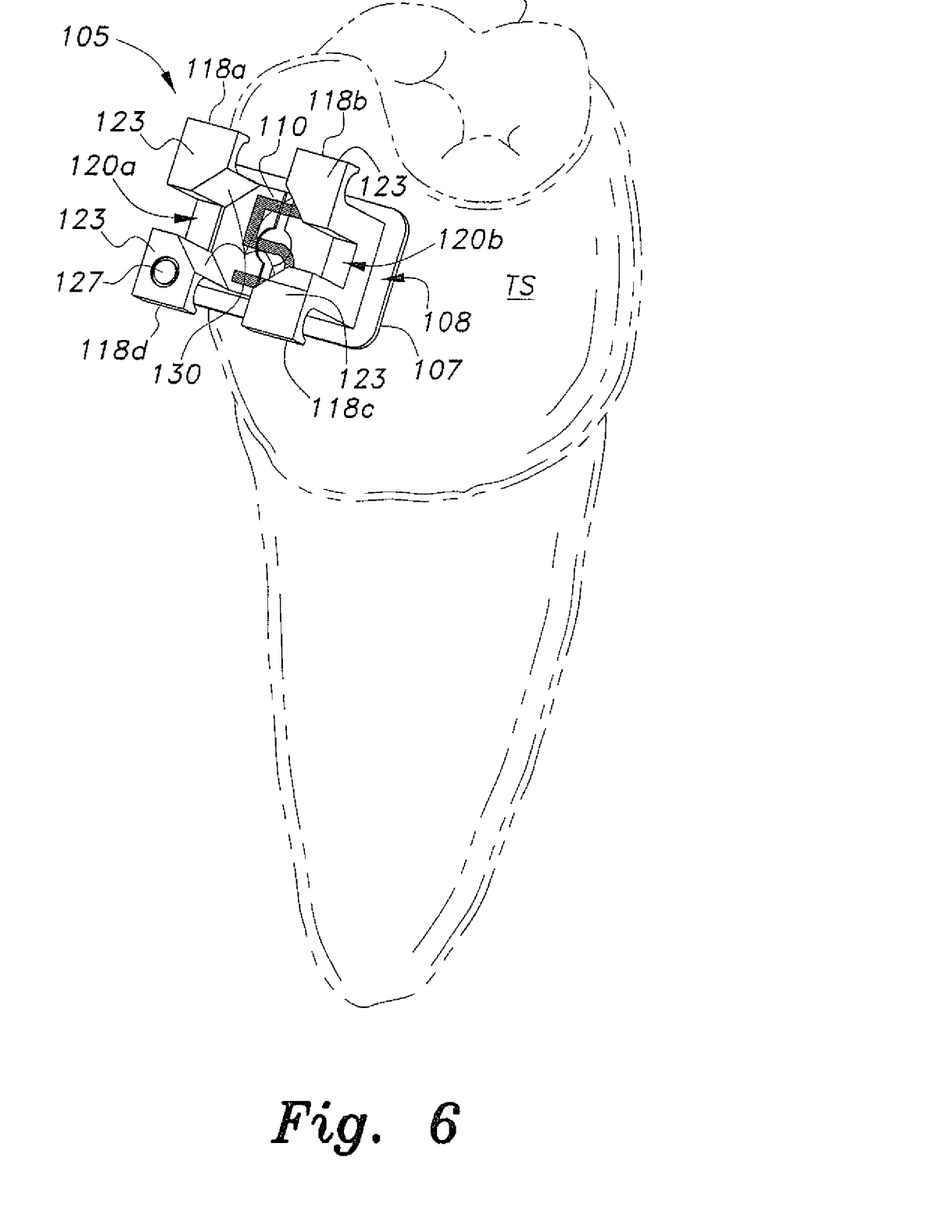
FIG. 6 illustrates a bracket coupled to a tooth, according to the present invention.
Figure 7:
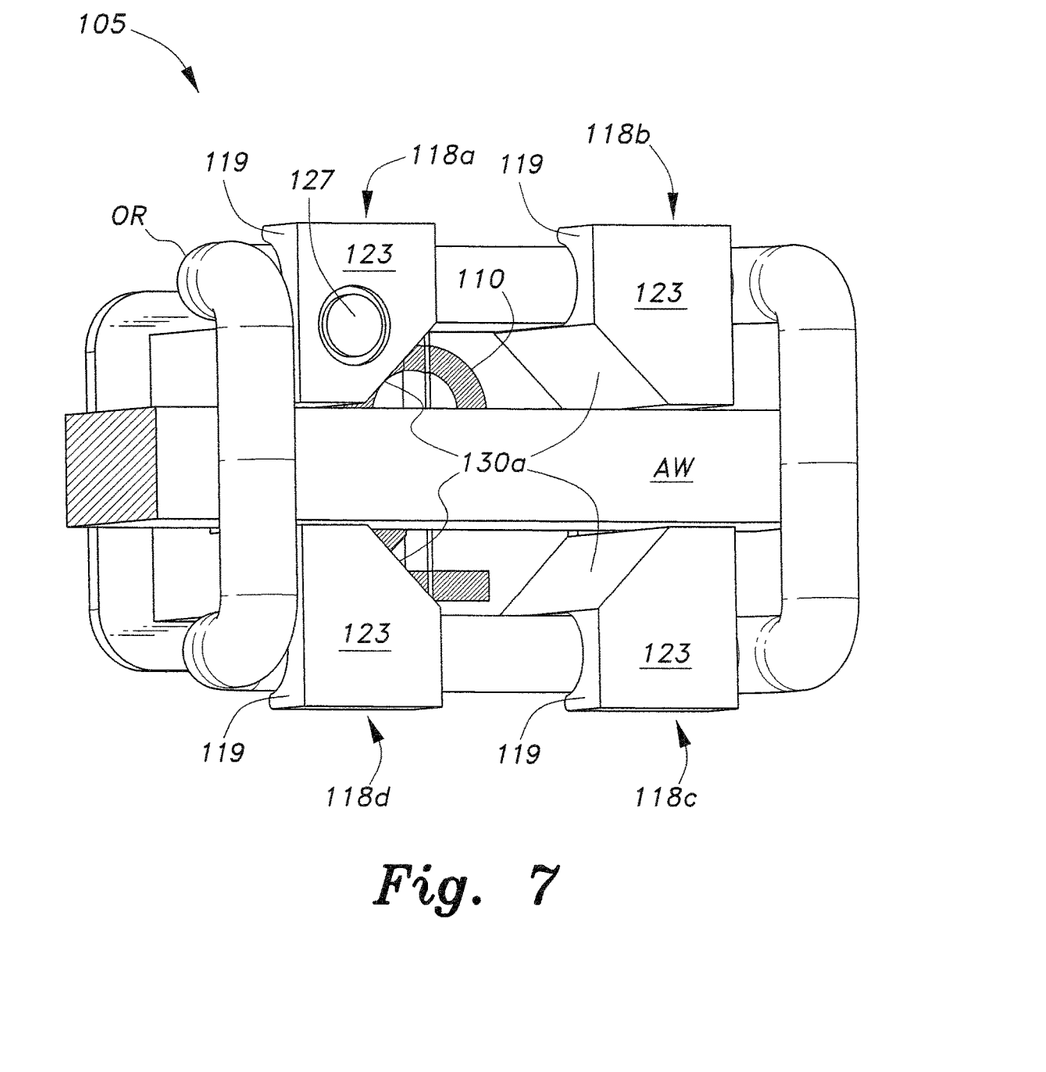
FIG. 7 is an illustration of an o-ring used to secure an archwire within the horizontal archwire slot, according to the present invention.
Figure 8:
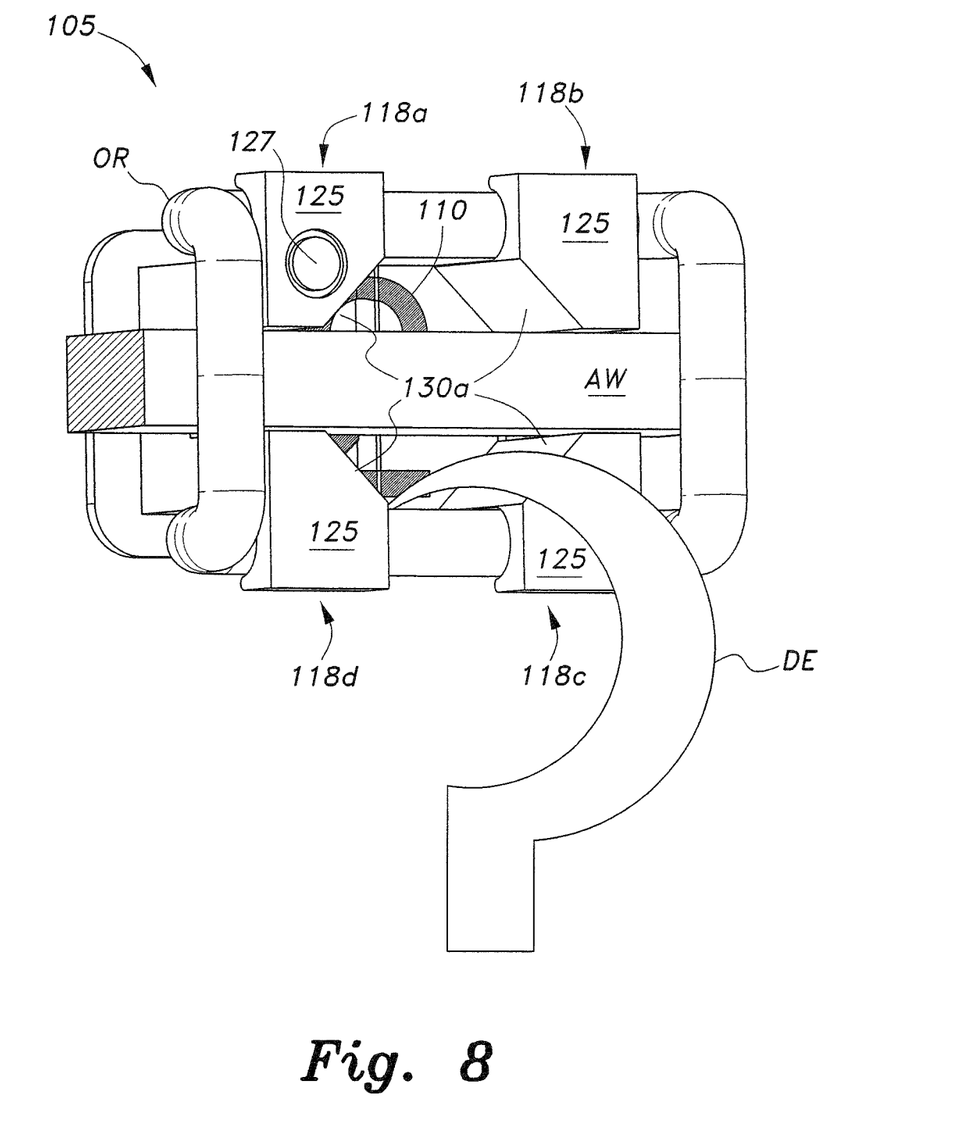
FIG. 8 is an illustration of the removal of an o-ring from the bracket, according to the present invention.

The lip 119 provides a hook for engaging auxiliary structures, such as an elastic o-ring OR, as illustrated in FIG. 6. The lip 119 and the configuration of the shaft inner sides 130, i.e., face-to-face configuration, can facilitate single tie-wing ligation for correcting rotated teeth or aligning highly located upper canines. The face-to-face configuration of the shaft inner sides 30 also facilitates insertion of a dental explorer between tie-wings for easy removal of the elastic O-ring OR (FIG. 7).

It is to be understood that the present invention is not limited to the embodiments described above, but encompasses any and all embodiments within the scope of the following claims.

We claim:

1. A set of orthodontic brackets adapted to move maloccluded teeth to proper positions within their respective quadrants, comprising:
  a plurality of orthodontic brackets, each of the brackets consists of:
  i) a base having a rear surface and a front surface, the rear surface of the base being configured for attachment onto a tooth surface;
  ii) a body extending from the front surface of the base, the body including a lower labial surface defined by an exposed, lower horizontal surface of the base and created by a plurality of tie-wings extending from corner portions of the base thereby forming an inter-tie-wings space, each of the plurality of tie-wings including a plurality of upright sides extending from the base and an exposed upper horizontal surface extending normal to the plurality of upright sides and defining an upper labial surface, an inner upright side of each tie-wing facing an inner upright side of a diagonally opposed tie-wing, wherein the plurality of tie-wings include a disto-gingival tie-wing, a mesio-gingival tie-wing, a mesio-occlusal tie-wing, and a disto-occlusal tie-wing, further wherein the inner upright side of each tie-wing facing an inner upright side of a diagonally opposed tie-wing is dimensioned and configured to remain outside of the exposed horizontal labial surface thereby defining an unobstructed horizontal labial surface;
  iii) the lower labial surface includes an occluso-gingival opening, the occluso-gingival opening extending longitudinally along the entire central portion of the lower labial surface and includes a centering guide opening extending from a central portion of the occluso-gingival opening and adapted to receive a bracket positioning key to manipulate bracket positioning prior to receiving a bonding agent;

iv) a first indicia only on the inter-tie-wings space, wherein the first indicia is a number in the sequence of the number of brackets and occupies substantially the entire inter-tie-wing space, wherein the first indicia constitutes a permanent marking on the inter-tie-wings space;

v) a single, second indicia only on the upper labial surface of disto-gingival tie-wing, the second indicia being non-numerical and being sequentially matched to a respective quadrant of the patient's mouth, wherein the second indicia constitutes a permanent marking on the upper labial surface; and vi) a pair of horizontally aligned archwire slots, each archwire slot being defined by a space between two tie-wings.

2. The orthodontic bracket according to claim 1, wherein each of the plurality of tie-wings includes a lip depending therefrom.

3. The orthodontic bracket according to claim 1, wherein the plurality of orthodontic brackets include eight.

4. The orthodontic bracket according to claim 3, wherein the plurality of brackets are thirty two divided into four groups corresponding to a respective quadrant.

* * * * *